United States Patent
Cheung et al.

(10) Patent No.: US 7,306,683 B2
(45) Date of Patent: Dec. 11, 2007

(54) SHAPE MEMORY MATERIAL AND METHOD OF MAKING THE SAME

(75) Inventors: Kenneth Man Chee Cheung, Hong Kong (CN); Kelvin Wai Kwok Yeung, Hong Kong (CN); William Weijia Lu, Hong Kong (CN); Chl Yuen Chung, Hong Kong (CN)

(73) Assignees: Versitech Limited, Hong Kong (CN); The City University of Hong Kong, Hong Kong (CN)

( * ) Notice: Subject to any disclaimer, the term of this patent is extended or adjusted under 35 U.S.C. 154(b) by 218 days.

(21) Appl. No.: 10/827,665

(22) Filed: Apr. 19, 2004

(65) Prior Publication Data

US 2004/0265614 A1 Dec. 30, 2004

Related U.S. Application Data

(60) Provisional application No. 60/464,083, filed on Apr. 18, 2003.

(51) Int. Cl.
*C22F 1/10* (2006.01)

(52) U.S. Cl. ...................... 148/563; 148/677
(58) Field of Classification Search ................ 148/563
See application file for complete search history.

(56) References Cited

U.S. PATENT DOCUMENTS

| 4,170,990 | A | | 10/1979 | Baumgart et al. | |
| 5,092,941 | A | * | 3/1992 | Miura | 148/563 |
| 5,190,546 | A | * | 3/1993 | Jervis | 606/78 |
| 5,611,874 | A | * | 3/1997 | Zadno-Azizi et al. | 148/402 |
| 5,641,364 | A | * | 6/1997 | Golberg et al. | 148/563 |

(Continued)

FOREIGN PATENT DOCUMENTS

JP 59-028548 A * 2/1984

(Continued)

OTHER PUBLICATIONS

Gil et al., Journal of Materials Science: Materials In Medicine, vol. 7, pp. 403-406 (1996).

(Continued)

*Primary Examiner*—George P. Wyszomierski
(74) *Attorney, Agent, or Firm*—Dickstein, Shapiro, LLP.

(57) ABSTRACT

The present invention relates generally to a shape memory and/or super-elastic material, such as a nickel titanium alloy. Additionally or alternatively, the present invention relates to a super-elastic or pseudo-elastic material that has an initial transition temperature $A_f$ above a body temperature. The shape memory material can have a super-elasticity or pseudo-elasticity property at a temperature below the initial transition temperature $A_f$ of the material. For example, the shape memory material can have its workable temperature for producing super-elasticity or pseudo-elasticity of about 0° C. to 15° C. below the initial transition temperature $A_f$. The shape memory material can be malleable at a room temperature, and become super-elastic or pseudo-elastic at a body temperature. In addition, the present invention relates to a method of making a shape memory or a super-elastic material. The treatment protocols can include but not limited to thermo-mechanical, thermo-mechanical, radiation, and ternary alloying treatments.

28 Claims, 4 Drawing Sheets

| No. of Specimen | 2nd Ageing Temperature (°C) | Time for 2nd Ageing (Min.) | Cooling Method | Austenite Phase Starting Temp. (°C) | Austenite Phase Peak Temp. (°C) | Austenite Phase Finish Temp. (°C) | Remarks |
|---|---|---|---|---|---|---|---|
| 20 | 250 | 30 | Water quench | 15 | 22.5 | 40 | |
| 21 | 300 | 30 | Water quench | 25 | 33.5 | 50 | |
| 22 | 300 | 40 | Water quench | 27 | 36 | 56 | |
| 23 | 300 | 60 | Water quench | 29 | 35.5 | 58 | Specimen Nos. 20 to 30 were subjected to solid solution treatment at 800°C for 1 hour and cooled down inside furnace. Then, these specimens were treated by ageing at 450°C for 0.75 hour and were then quenched by water. |
| 24 | 350 | 30 | Water quench | 29.5 | 35 | 53 | |
| 25 | 350 | 40 | Water quench | 32 | 38.5 | 60 | |
| 26 | 350 | 60 | Water quench | 38.5 | 45 | 65 | |
| 27 | 400 | 30 | Water quench | 35 | 42 | 43 | |
| 28 | 400 | 40 | Water quench | 42.5 | 48.5 | 64 | |
| 29 | 400 | 60 | Water quench | 38.5 | 45 | 61 | |
| 30 | 250 | 30 | Water quench | 15 | 22.5 | 40 | |

U.S. PATENT DOCUMENTS

| | | | |
|---|---|---|---|
| 6,096,175 A * | 8/2000 | Roth | 204/192.15 |
| 6,127,597 A | 10/2000 | Beyar et al. | |
| 6,224,600 B1 | 5/2001 | Protogirou | |
| 6,235,031 B1 | 5/2001 | Hodgeman et al. | |
| 6,306,141 B1 | 10/2001 | Jervis | |
| 6,375,458 B1 * | 4/2002 | Moorleghem et al. | 433/2 |
| 6,416,544 B2 * | 7/2002 | Sugita et al. | 623/1.19 |
| 7,192,496 B2 * | 3/2007 | Wojcik | 148/675 |
| 2002/0129822 A1 * | 9/2002 | Furukawa et al. | 128/887 |

FOREIGN PATENT DOCUMENTS

| | | | |
|---|---|---|---|
| JP | 60-103166 A | * | 6/1985 |
| JP | 61-276947 A | * | 12/1986 |
| JP | 01310664 | | 6/1988 |
| JP | 04-141562 A | * | 5/1992 |

OTHER PUBLICATIONS

Miyazaki et al., Acta metall., vol. 34, pp. 2045-2051 (1986).
Liu et al., Materials Transactions, JIM, vol. 37, pp. 691-696 (1996).
Sadrnezhaad et al., Materials and Manufacturing Processes, vol. 12, pp. 107-115 (1997).
Liu et al., Journal of Materials Science, vol. 32, pp. 5979-5984 (1997).
T. Saburi, "Ti-Ni shape memory alloys", Shape Memory Materials, Cambrdige University Press, pp. 49-96 (1999).
Gil et al., "Thermal Cycling and Ageing Effects in Ni-Ti Shape Memory Alloys Used in Biomedical Applications", 11th Conference of the ESB, Toulouse, France (Jul. 1998).

* cited by examiner

| No. of Specimen | Solid Solution Temperature (°C) | Time for Solid Solution (Hours) | Cooling Method | Ageing Temperature (°C) | Time for Ageing (Hours) | Cooling Method | Austenite Phase Starting Temp. (°C) | Austenite Phase Peak Temp. (°C) | Austenite Phase Finish Temp. (°C) |
|---|---|---|---|---|---|---|---|---|---|
| 1 | 800 | 1 | Inside furnace | 450 | 0.5 | Water quench | 26 | 33.5 | 47 |
| 2 | 800 | 1 | Inside furnace | 400 | 0.5 | Water quench | 26 | 29 | 52 |
| 3 | 800 | 1 | Inside furnace | 400 | 0.5 | Inside furnace | 37.5 | 41 | 58 |
| 4 | 800 | 1 | Water quench | 450 | 0.5 | Water quench | 26.5 | 33 | 58 |
| 5 | 800 | 1 | Inside furnace | 450 | 0.5 | Water quench | 26 | 33.5 | 47 |
| 6 | 800 | 1 | Inside furnace | 450 | 0.5 | Inside furnace | 30.5 | 36.5 | 48 |
| 7 | 800 | 1 | Inside furnace | 450 | 0.75 | Water quench | 16 | 22.5 | 44 |
| 8 | 800 | 1 | Inside furnace | 450 | 0.75 | Inside furnace | 35 | 39 | 56 |
| 9 | 800 | 1 | Inside furnace | 460 | 0.5 | Inside furnace | 35.5 | 39 | 47 |
| 10 | 800 | 1 | Inside furnace | 460 | 0.75 | Inside furnace | 34 | 36.5 | 60 |
| 11 | 800 | 1 | Inside furnace | 480 | 0.5 | Inside furnace | 29 | 33 | 55 |
| 12 | 800 | 1 | Inside furnace | 480 | 0.75 | Inside furnace | 29 | 35 | 54 |
| 13 | 800 | 1 | Inside furnace | 500 | 0.5 | Water quench | 30 | 36 | 50 |
| 14 | 800 | 1 | Inside furnace | 500 | 0.25 | Inside furnace | 12 | 32 | 43 |
| 15 | 800 | 1 | Inside furnace | 500 | 0.33 | Inside furnace | 27 | 34 | 45 |
| 16 | 800 | 1 | Inside furnace | 500 | 0.5 | Inside furnace | 29 | 34 | 45 |
| 17 | 800 | 1 | Inside furnace | 520 | 0.5 | Inside furnace | 10 | 28 | 42 |
| 18 | 850 | 1 | Water quench | 450 | 0.5 | Water quench | 31.5 | 34.5 | 72 |
| 19 | 900 | 1 | Inside furnace | 450 | 0.5 | Inside furnace | 27 | 34 | 57 |

Fig. 1

| No. of Specimen | 2nd Ageing Temperature (°C) | Time for 2nd Ageing (Min.) | Cooling Method | Austenite Phase Starting Temp. (°C) | Austenite Phase Peak Temp. (°C) | Austenite Phase Finish Temp. (°C) | Remarks |
|---|---|---|---|---|---|---|---|
| 20 | 250 | 30 | Water quench | 15 | 22.5 | 40 | Specimen Nos. 20 to 30 were subjected to solid solution treatment at 800°C for 1 hour and cooled down inside furnace. Then, these specimens were treated by ageing at 450°C for 0.75 hour and were then quenched by water. |
| 21 | 300 | 30 | Water quench | 25 | 33.5 | 50 | |
| 22 | 300 | 40 | Water quench | 27 | 36 | 56 | |
| 23 | 300 | 60 | Water quench | 29 | 35.5 | 58 | |
| 24 | 350 | 30 | Water quench | 29.5 | 35 | 53 | |
| 25 | 350 | 40 | Water quench | 32 | 38.5 | 60 | |
| 26 | 350 | 60 | Water quench | 38.5 | 45 | 65 | |
| 27 | 400 | 30 | Water quench | 35 | 42 | 43 | |
| 28 | 400 | 40 | Water quench | 42.5 | 48.5 | 64 | |
| 29 | 400 | 60 | Water quench | 38.5 | 45 | 61 | |
| 30 | 250 | 30 | Water quench | 15 | 22.5 | 40 | |

Fig. 2

| No. of Specimen | 2nd Ageing Temperature (°C) | Time for 2nd Ageing (Min.) | Cooling Method | Austenite Phase Starting Temp. (°C) | Austenite Phase Peak Temp. (°C) | Austenite Phase Finish Temp. (°C) | Remarks |
|---|---|---|---|---|---|---|---|
| 31 | 200 | 30 | Inside furnace | 22 | 33 | 43 | Specimen Nos. 31 to 42 were subjected to solid solution treatment at 800°C for 1 hour and cooled down inside furnace. Then, these specimens were treated by ageing at 500°C for 0.5 hour and were then cooled inside furnace. |
| 32 | 200 | 30 | Water quench | 21 | 30 | 40 | |
| 33 | 200 | 60 | Inside furnace | 13 | 27.5 | 40 | |
| 34 | 200 | 60 | Water quench | 27 | 35 | 47 | |
| 35 | 300 | 30 | Inside furnace | 7 | 28 | 50 | |
| 36 | 300 | 30 | Water quench | 18 | 29 | 41 | |
| 37 | 300 | 60 | Inside furnace | 15 | 31.5 | 44 | |
| 38 | 300 | 60 | Water quench | 26 | 36.5 | 44 | |
| 39 | 400 | 30 | Inside furnace | 31 | 44 | 60 | |
| 40 | 400 | 30 | Water quench | 26 | 38 | 52 | |
| 41 | 400 | 60 | Inside furnace | 35 | 49 | 64 | |
| 42 | 400 | 60 | Water quench | 27 | 42.5 | 56 | |

Fig. 3

SHAPE MEMORY MATERIAL AND METHOD OF MAKING THE SAME

CROSS-REFERENCE TO RELATED APPLICATION

This patent application claims benefit of U.S. Provisional Patent Application No. 60/464,083 filed Apr. 18, 2003.

TECHNICAL FIELD

The present invention relates generally to a shape memory material. More specifically, the present invention relates to a super-elastic or pseudo-elastic material that has an initial transition temperature $A_f$ above a body temperature. In addition, the present invention relates to a method of making the shape memory material.

BACKGROUND OF THE INVENTION

Nickel titanium (NiTi) alloys have the properties of shape memory effect and super-elasticity. The shape-memory phenomenon, first found nearly half a century ago, is that a material can exhibit one shape at a cold temperature and another shape after being heated to a higher temperature. The material is in its original shape at the higher temperature. When being cooled to a lower temperature, the material retains its original shape but changes the structure to martensite, where the material can be easily deformed into different shapes at the lower temperature. Upon heating, the material changes back to austenite, where the deformation is recovered and the shape is restored (one-way shape memory). Alloys can also have two memories (two-way shape memory) that exhibit a reversible effect, with heat causing the change in shape which can be reversed by cooling. The phase that is stable at the lower temperature is called Martensite (B19'); the phase stable at the higher temperature is called Austenite (B2).

The shape memory effect (SME) results from thermoelastic martensitic transition. Martensite is produced when austenite crystals in the parent matrix are cooled below the martensitic phase transition starting temperature ($M_s$). No macro shape change occurs at this stage, because of the formation of martensite twin in a self-accommodation structure. Twin boundaries can move and disappear when the martensite gains increased stress at a temperature below the martensitic phase transition finishing temperature ($M_f$), leading to macro deformation. The deformed martensite can be restored to the original shape of the parent phase through reverse transformation (from martensite to austenite) when being heated to a temperature above the austenitic phase transition starting temperature ($A_s$). Sometimes, martensitic reorientation can occur if the martensitic phase in the matrix is under increased stress. This phenomenon greatly contributes to the shape memory effect.

Super-elasticity (SE) or pseudo-elasticity (PE) occurs when a shape memory alloy shows a good performance at a temperature above the austenitic phase transition finishing temperature $A_f$ and is deformed at a temperature above $M_s$. For example, the best workable temperature range for PE is 10° C. to 15° C. above the $A_f$. This effect is caused by the stress-induced martensite (SIM) formed at a temperature above $M_s$. As martensite is formed with stress applied thereto, the martensite reverts immediately to the undeformed austenite when the stress is removed. This process produces a "rubber-like" behavior in these alloys. This material will show two plateaus on the stress-strain curve in a tensile or compression testing, one in the upper (loading) section and the other in the lower (unloading) section, which are the regions of super-elasticity.

SUMMARY OF THE INVENTION

The present invention can provide a shape memory material that has its workable temperature range of super-elasticity of about 0° C. to 15° C. below the initial transition temperature $A_f$ of the material. For example, the shape memory material can be a heat-treated NiTi alloy. The physical properties of the shape memory material are such that the material is malleable at room temperature, but becomes super-elastic or pseudo-elastic at a body temperature. The shape memory material can be used in various applications, including but not limited to, orthopedic implants.

The present invention can also provide a method of making a shape memory material. The method can comprise treating a raw material at a temperature ranging from about 700° C. to 900° C. for a time period of about 0.5 to 2 hours. The heat-treated raw material can be cooled by various means, such as by air or water or inside furnace. The treated raw material can be subjected to an ageing treatment at a temperature ranging from about 200° C. to about 520° C. for a time period of about 0.25 to 2 hours to provide a shape memory material. The shape memory material can be cooled by various means, such as by air or water or inside furnace.

Optionally, the method can comprise a second ageing treatment of the material at a temperature ranging from about 200° C. to about 500° C. for a time period of about 0.5 to 2 hours followed by a cooling process, such as by air or water or inside furnace.

BRIEF DESCRIPTION OF THE DRAWINGS

The detailed description of the present invention will be better understood in conjunction with the accompanying drawings, which are for illustrative purposes only. The present invention is not limited to the exemplary embodiments shown in such drawings.

FIG. 1 shows various thermal treatment protocols for adjusting the initial transition temperature $A_f$ of the solid solution to be above a body temperature.

FIG. 2 shows various protocols of a second ageing treatment of the solid solution.

FIG. 3 shows various alternative protocols of a second ageing treatment of the solid solution.

DETAILED DESCRIPTION OF THE INVENTION

Figure 4:
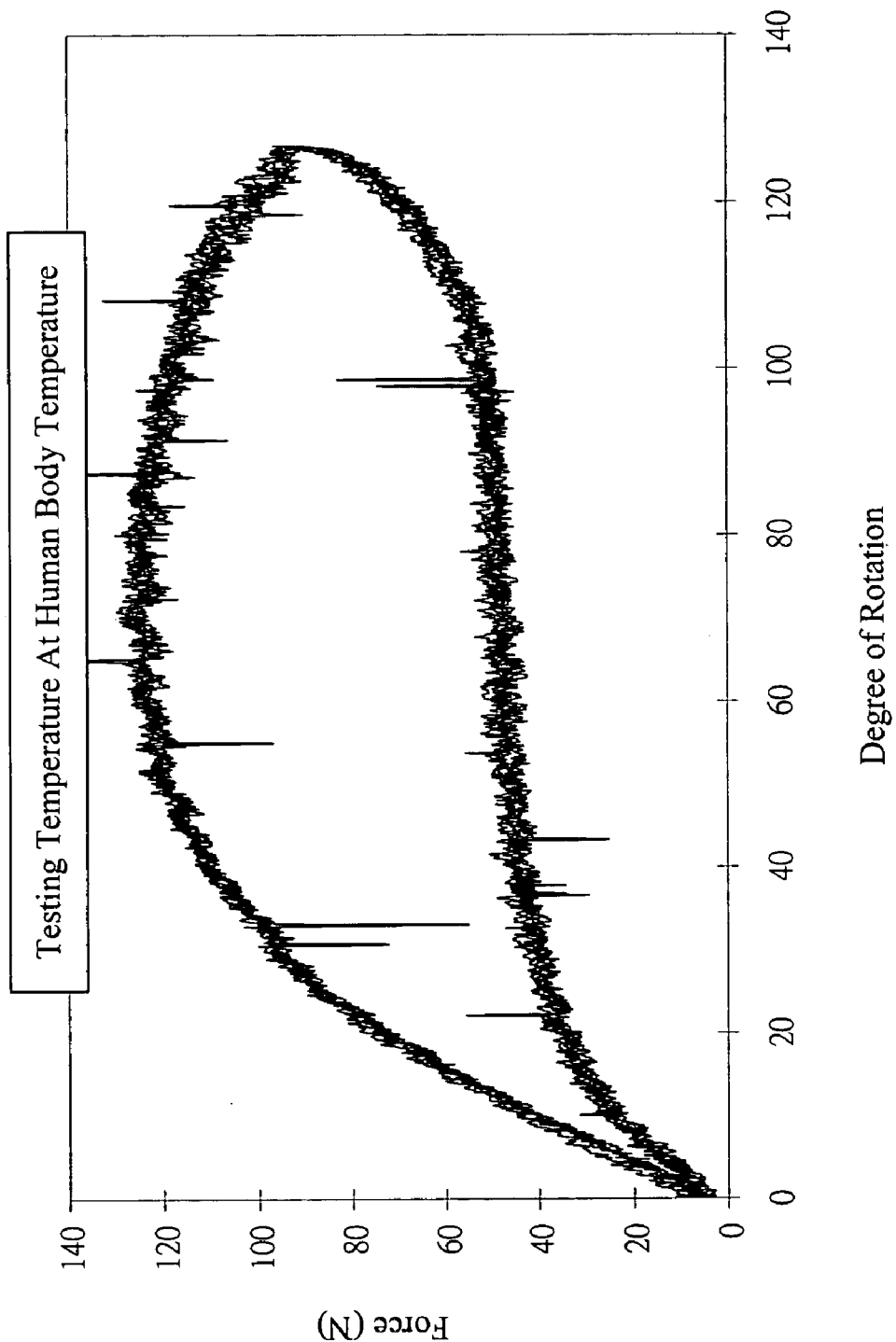
FIG. 4 shows the mechanical testing result of Specimen No. 5 having super-elasticity at a human body temperature (e.g., 96° F. to 99° F.).

For the purposes of promoting an understanding of the principles of the present invention, various exemplary embodiments will be illustrated and discussed in great details in connection with the accompanying drawings. In particular, various thermal treatment protocols will be discussed, which facilitate to utilize or maximize the super-elasticity or pseudo-elasticity of the shape memory material, such as a nickel titanium alloy, at a human body temperature.

The present invention can provide a new material, which can have a shape memory effect. The shape memory effect enables a material to return to a predetermined shape upon heating or cooling via a phase transformation. For example, the material can have a shape memory effect at a body temperature, such as a human body temperature. Additionally or alternatively, the present invention can provide a new material, which can have a super-elasticity or pseudo-elasticity property. The super-elastic or pseudo-elastic property of a material means that a constant force or similar forces can be obtained when the material is mechanically or physically deformed beyond its elastic limit but within its plastic limit. Such a force can be kept constant or substantially constant during the deformation process. For example, the material can have a super-elasticity or pseudo-elasticity at a body temperature, such as a human body temperature.

In one exemplary embodiment, the shape memory material can have an initial transition temperature $A_f$ above a body temperature, such as a human body temperature. For example, the normal range of human body temperature is in the range of about 36.1° C. to about 37.8° C. In an exemplary embodiment, the material can have an initial transition temperature $A_f$ in the range of about 36° C. to about 72° C. In an exemplary embodiment, the material can have an initial transition temperature $A_f$ of about 0° C. to about 15° C. above a body temperature, without any stress loading to the material. For example, the material can have an initial transition temperature $A_f$ in the range of about 36° C. to about 53° C. In another exemplary embodiment, the material can have an initial transition temperature $A_f$ of about 10° C. to about 15° C. above a body temperature. For example, the material can have an initial transition temperature $A_f$ in the range of about 46° C. to about 53° C.

In another embodiment, the present invention can provide a material with a super-elasticity or pseudo-elasticity property. In an exemplary embodiment, the material can have a super-elasticity or pseudo-elasticity at a body temperature. In another exemplary embodiment, the material can be malleable at a room temperature but change to a super-elasticity or pseudo-elasticity phase at a human body temperature.

The material can have various forms and/or compositions. For example, the material can be in the form of an alloy. In an exemplary embodiment, the material can comprise a nickel titanium alloy. In another exemplary embodiment, the material can comprise an equiatomic nickel titanium alloy, such as having a nickel to titanium ratio of about 50% to 50%. It will be appreciated that other forms and/or compositions of the material are also within the scope of the present invention.

According to another aspect of the present invention, various articles can be formed of the shape memory and/or super-elastic material. For example, the articles can be structural components of various shapes, such as rod, cylindrical, square, hexagonal, or other shapes or a combination of above shapes. Additionally or alternatively, the shape memory and/or super-elastic material can have various applications, including but not limited to, various medical uses such as orthopedic implants. For example, the shape memory material and/or the nickel titanium alloy can be made into various plates, rods, wires, screws, or a combination of the above as implants to be applied to a patient's bone or other tissues or organs. It will be appreciated that other applications of the shape memory and/or super-elastic material are also within the scope of the present invention.

In one embodiment, the article or structural component formed of the shape memory and/or super-elastic material can have shape memory property and/or super-elasticity. For example, the article or structural component can be super-elastic and capable of providing a substantially constant or similar forces. In an exemplary embodiment, the article can be in the form of a medical implant and provide a constant force for bone fixation. In one exemplary embodiment, such constant force can be determined or controlled in various ways to reinforce or reduce the force generated by the material. For example, the constant force can be determined by the size or number of the article used, the composition of the material, thermal treatment, thermal mechanical treatment, ternary alloying, radiation treatment of the material, and any combination of the above. It will be appreciated that other treatments for determining or controlling the constant force are also within the scope of the present invention.

According to a further aspect of the present invention, a method can be provided for making a shape memory and/or super-elastic material. For example, one or more of thermal treatment, thermal-mechanical treatment, radiation, ternary alloying, and the like can be used. In an exemplary embodiment, a thermal treatment can be used to form the shape memory and/or super-elastic material. It will be appreciated that various other treatments and/or combinations of treatments are also within the scope of the present invention. Optionally, one or more additional mechanical treatments, such as compression, tensile, bending, torsion, cold working, hot working, and the like can be used for making the shape memory and/or super-elastic material.

In one embodiment, the method can comprise a solid solution treatment and an ageing treatment of a raw material. In an exemplary embodiment, the raw material can be any alloy, such as a nickel titanium alloy. In a solid solution treatment, the raw material can be heated to a temperature near the crystallization temperature of the raw material. The elevated temperature can cause atomic diffusion, recrystallization, and/or precipitation. The treated material can be subjected to cooling by various conventional methods and/or the ageing treatment to form the shape memory material having an initial transition temperature $A_f$ above a body temperature.

In one exemplary embodiment, the solid solution treatment of the raw material can be carried out at a temperature ranging from about 700° C. to about 900° C. In an exemplary embodiment, the raw material is treated at a temperature ranging from about 800° C. to about 900° C. In another exemplary embodiment, the raw material is treated at about 800° C. Additionally or alternatively, the solid solution treatment can last for a time period of about 0.5 to 2 hours. It will be appreciated that various other embodiments of the solid solution treatment are also within the scope of the present invention.

In another exemplary embodiment, the treated raw material can be cooled by various conventional methods, such as by air or water or inside furnace. For example, the treated raw material can be quenched by water. It will be appreciated that various other embodiments of the cooling treatment are also within the scope of the present invention.

In a further exemplary embodiment, the ageing treatment of the treated raw material can be carried out at a temperature ranging from about 200° C. to about 520° C. to obtain the shape memory or super-elastic material. In an exemplary embodiment, the ageing treatment can be carried out at a temperature ranging from about 250° C. to about 500° C. Additionally or alternatively, the ageing treatment is carried out for a time period of about 0.25 to 2 hours. In an exemplary embodiment, the ageing treatment is carried out for a time period of about 0.5 to 2 hours. It will be appreciated that various other embodiments of the ageing treatment are also within the scope of the present invention.

Optionally, a second ageing treatment can be provided to reinforce the super-elasticity or pseudo-elasticity of the shape memory material. In an exemplary embodiment, the second ageing treatment can be carried out at a temperature from about 200° C. to about 500° C. In another exemplary embodiment, the second ageing treatment can be carried out at a temperature from about 250° C. to about 500° C. Additionally or alternatively, the second ageing treatment can be carried out for about 0.5 to 2 hours. In an exemplary embodiment, the second ageing treatment can be carried out for about 0.5 to 1 hour. It will be appreciated that various other embodiments of the second ageing treatment are also within the scope of the present invention.

The present invention can further provide a material formed according to the above method. In an exemplary embodiment, the material can have an initial transition temperature $A_f$ above a body temperature. For example, the material can have an initial austenite phase finishing temperature of about 0° C. to 15° C. above a body temperature. In one exemplary embodiment, the material can comprise a nickel titanium alloy. For example, the NiTi alloy can have a nickel to titanium ratio of about 50% to 50%.

FIG. 1 illustrates various exemplary thermal treatment protocols, where the solid solution temperature, ageing temperature, time for treatment and cooling method are shown. In addition, the austenite phase starting temperature, peak temperature, and finish temperature of each specimen are also shown. In one exemplary embodiment, Specimen No. 5 can be treated at the temperature of about 800° C. for about one hour. The solid solution so treated can be cooled inside furnace. The treated solid solution can be subjected to an ageing treatment at the temperature of about 450° C. for about half an hour and then be quenched by water. The material so formed can have an initial austenite phase starting temperature of about 26° C., an initial austenite phase peak temperature of about 33.5° C., and an initial austenite phase finish temperature of about 47° C.

In another exemplary embodiment, Specimen No. 7 can be treated at the temperature of about 800° C. for about one hour and cooled inside furnace. The treated solid solution can be subjected to an ageing treatment at about 450° C. for about 0.75 hour and quenched by water. The resulting material can have an initial austenite phase starting temperature of about 16° C., an initial austenite phase peak temperature of about 22.5° C., and an initial austenite phase finish temperature of about 44° C.

In a further exemplary embodiment, Specimen No. 14 can be treated at the temperature of about 800° C. for about one hour and cooled down inside furnace. The treated solid solution can be subjected to an ageing treatment at the temperature of about 500° C. for about half an hour and then cooled inside furnace. The material so formed can have an initial austenite phase starting temperature of about 12° C., an initial austenite phase peak temperature of about 32° C., and an initial austenite phase finish temperature of about 43° C.

FIGS. 2 and 3 show various alternative thermal treatment protocols. For example, various Specimen Nos. 20 to 40 can be first subjected to a thermal treatment protocol, such as one of those shown in FIG. 1. In the various exemplary embodiments shown in FIG. 2, Specimen Nos. 20 to 30 can be first subjected to a thermal treatment protocol of Specimen No. 7 as described above. Specimen Nos. 20 to 30 can then be subjected to various types of second ageing treatment, such as those illustrated in FIG. 2. For example, Specimen No. 21 can be subjected to a second ageing treatment at the temperature of about 300° C. for about half an hour and then quenched by water. The resulting material can have an initial austenite phase starting temperature of about 25° C., an initial austenite phase peak temperature of about 33.5° C., and an initial austenite phase finish temperature of about 50° C.

In another exemplary embodiments shown in FIG. 3, Specimen Nos. 31 to 42 can be first subjected to a thermal treatment protocol of Specimen No. 14 as described above. Specimen Nos. 31 to 42 can then be subjected to various types of second ageing treatment, such as those illustrated in FIG. 3. For example, Specimen No. 38 can be subjected to a second ageing treatment at the temperature of about 300° C. for about one hour and then quenched by water. The resulting material can have an initial austenite phase starting temperature of about 26° C., an initial austenite phase peak temperature of about 36.5° C., and an initial austenite phase finish temperature of about 44° C.

FIG. 4 shows the mechanical testing results of Specimen No. 5. The initial transition temperature $A_f$ of this Specimen is 10° C. above the human body temperature, while super-elasticity or pseudo-elasticity is seen at the human body temperature.

While various thermal treatment protocols have been illustrated to make a shape memory and/or super-elastic material and/or adjust the initial transition temperature $A_f$ of the shape memory and/or super-elastic material to be above a body temperature, it will be appreciated that various other protocols for adjusting the initial transition temperature $A_f$ are also within the scope of the present invention.

It will be appreciated that the various features described herein may be used singly or in any combination thereof. Therefore, the present invention is not limited to only the embodiments specifically described herein. While the foregoing description and drawings represent a preferred embodiment of the present invention, it will be understood that various additions, modifications, and substitutions may be made therein without departing from the spirit of the present invention. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive.

What is claimed is:

1. A method of making a super-elastic or pseudo-elastic material, the method comprising:
   providing a raw material; and
   heat treating the raw material to obtain a heat-treated raw material;
   subjecting the heat-treated raw material to first and second ageing treatments; and
   cooling the heat-treated raw material after each of the ageing treatments;
   wherein the super-elastic or pseudo-elastic material formed has an initial transition temperature $A_f$ above a body temperature.

2. The method of claim 1, wherein each aging treatment is selected from the group consisting of thermo-treatment, thermo-mechanical treatment, radiation treatment, and any combination thereof.

3. The method of claim 1 further comprising a mechanical treatment selected from the group consisting of compression, tensile, bending, torsion cold working, hot working, and any combination thereof.

4. The method of claim 1, wherein the initial transition temperature $A_f$ is about 0° C. to about 15° C. above a body temperature.

5. The method claim 1, wherein the super-elastic or pseudo-elastic material is malleable at a room temperature.

6. The method of claim 1, wherein the super-elastic or pseudo-elastic material is super-elastic or pseudo-elastic at a body temperature.

7. The method of claim 1, wherein the raw material is heated at a temperature ranging from about 700° C. to about 900° C. for a rime period of about 0.5 to 2 hours.

8. The method of claim 7, wherein the heat-treated raw material is subjected to an ageing treatment at a temperature ranging from about 200° C. to about 520° C. for a time period of about 0.25 to 2 hours.

9. The method of claim 8, wherein the ageing treatment is carried out at a temperature ranging from about 250° C. to about 500° C.

10. The method of claim 8, further comprising a second ageing treatment which is carried out at a temperature ranging from about 200° C. to about 500° C. for a time period of about 0.5 to 2 hours.

11. The method of claim 10, wherein the second ageing treatment is carried out at a temperature ranging from about 250° C. to about 500° C.

12. The method of claim 10, wherein the second ageing treatment is carried out for a time period of about 0.5 to 1 hour.

13. The method of claim 1, wherein the raw material is heated at a temperature ranging from about 800° C. to about 900° C.

14. The method of claim 1, further comprising subjecting the raw material to ternary alloying.

15. A method of making a super-elastic or pseudo-elastic material, comprising:
    heating a raw material at a temperature ranging from about 700° C. to about 900° C. for a time period of about 0.5 to 2 hours to obtain a heat-treated raw material;
    subjecting the heat-treated raw material to an ageing treatment at a temperature ranging from about 200° C. to about 520° C. for a time period of about 0.25 to 2 hours; and
    cooling tile heat-treated raw material after the heating treatment and the ageing treatment inside furnace or by water quench;
    wherein the super-elastic or pseudo-elastic material formed has super-elasticity at a body temperature.

16. The method of claim 15, wherein the raw material is heated at a temperature ranging from about 800° C. to about 900° C.

17. The method of claim 15, wherein the ageing treatment is carried out at a temperature ranging from about 250° C. to about 500° C.

18. The method of claim 15, wherein the ageing treatment is carried out for a time period of about 0.5 to 2 hours.

19. The method of claim 15, wherein the super-elastic or pseudo-elastic material has an initial austenite phase finishing temperature of about 0° C. to about 15° C. above a body temperature.

20. The method of claim 15, further comprising a second ageing treatment which is carried out at a temperature ranging from about 200° C. to about 500° C. for a time period of about 0.5 to 2 hours.

21. The method of claim 20, wherein the second ageing treatment is carried out at a temperature ranging from about 250° C. to about 500° C.

22. The method of claim 20, wherein the second ageing treatment is carried out for a time period of about 0.5 to 1 hour.

23. The method of claim 15, wherein the ageing treatment comprises first and second ageing treatments.

24. The method of claim 23, wherein the heat-treated raw material is cooled after each of the first and second ageing treatments.

25. A method of making a super-elastic or pseudo-elastic material, comprising:
    heating a raw material to obtain a heat-treated raw material;
    subjecting the heat-treated raw material to first and second ageing treatments; and
    cooling the treated raw material after heat treatment and each ageing treatment;
    wherein the super-elastic or pseudo-elastic material formed has super-elasticity at a body temperature.

26. The method of claim 25, wherein the heat-treated raw material is cooled inside furnace or by water quench.

27. The method of claim 25, wherein the super-elastic or pseudo-elastic material has an initial transition temperature $A_f$ about 0° C. to about 15° C. above a body temperature.

28. The method of claim 25, wherein, the super-elastic or pseudo-elastic material is malleable at a room temperature.

* * * * *

UNITED STATES PATENT AND TRADEMARK OFFICE
CERTIFICATE OF CORRECTION

| | |
|---|---|
| PATENT NO. | : 7,306,683 B2 |
| APPLICATION NO. | : 10/827665 |
| DATED | : December 11, 2007 |
| INVENTOR(S) | : Man Chee Kenneth Cheung et al. |

Page 1 of 1

It is certified that error appears in the above-identified patent and that said Letters Patent is hereby corrected as shown below:

Title Page should read

(75)    Inventors:    Kenneth Man Chee Cheung, Hong Kong (CN);
Kelvin Wai Kwok Yeung, Hong Kong (CN);
William Weijia Lu, Hong Kong (CN);
Chi Yuen Chung, Hong Kong (CN)

Signed and Sealed this

Tenth Day of June, 2008

JON W. DUDAS
*Director of the United States Patent and Trademark Office*